(12) United States Patent
Graf et al.

(10) Patent No.: US 9,205,189 B2
(45) Date of Patent: Dec. 8, 2015

(54) RESERVOIR MODULE COMPRISING A PISTON ROD

(71) Applicant: TECPHARMA LICENSING AG, Burgdorf (CH)

(72) Inventors: Roney Graf, Burgdorf (CH); Fritz Kirchhofer, Sumiswald (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 14/568,701

(22) Filed: Dec. 12, 2014

(65) Prior Publication Data
US 2015/0151043 A1    Jun. 4, 2015

Related U.S. Application Data

(60) Continuation of application No. 11/836,474, filed on Aug. 9, 2007, now Pat. No. 8,939,944, which is a division of application No. 10/767,974, filed on Jan. 29, 2004, now Pat. No. 7,628,773, which is a continuation of application No. PCT/CH02/00411, filed on Jul. 22, 2002.

(30) Foreign Application Priority Data

Jul. 30, 2001  (DE) ............................. 201 12 501 U
Dec. 21, 2001  (DE) ................................. 101 63 327

(51) Int. Cl.
*A61M 5/00*    (2006.01)
*A61M 5/145*   (2006.01)
(Continued)

(52) U.S. Cl.
CPC ............... *A61M 5/1456* (2013.01); *A61B 5/00* (2013.01); *A61M 5/1454* (2013.01);
(Continued)

(58) Field of Classification Search
CPC .............. A61M 5/24; A61M 5/31593; A61M 2005/2411; A61M 2005/3126; A61M 5/31541; A61M 5/31543; A61M 5/31551
USPC ................................... 604/207–211, 232–234
See application file for complete search history.

(56) References Cited

U.S. PATENT DOCUMENTS 4,498,904 A * 2/1985 Turner .................... A61M 5/24
422/928
4,592,745 A    6/1986 Rex et al.
(Continued)

FOREIGN PATENT DOCUMENTS

DE      3715340      11/1988
DE      4112259      10/1992
(Continued)

*Primary Examiner* — Phillip Gray
(74) *Attorney, Agent, or Firm* — Dorsey & Whitney LLP; Stuart R. Hemphill, Esq.

(57) ABSTRACT

A product dispensing apparatus including a reservoir module, a dosing module and a dose setting member. The reservoir module includes a front casing section, a block, a first connector, a piston, and a piston rod moveable in a dispensing movement and against the dispensing movement, and including a return block engageable with the block, wherein engagement between the block and the return block prevents the piston rod from moving against the dispensing movement. The dosing module includes a rear casing section, including a second connector which is engageable with the first connector to form a detachable connection between the reservoir module and the dosing module, and a dosing and drive device. The dose setting member engages the piston rod such that it is moveable together with and in the same direction as the piston rod during the dispensing movement and is moveable relative to the piston rod against the dispensing movement.

19 Claims, 9 Drawing Sheets

(51) Int. Cl.
  *A61B 5/00*    (2006.01)
  *A61M 5/168*   (2006.01)
  *A61M 5/24*    (2006.01)
  *A61M 5/315*   (2006.01)

(52) U.S. Cl.
  CPC ......... *A61M 5/16877* (2013.01); *A61M 5/315* (2013.01); *A61M 5/31553* (2013.01); *A61M 5/14566* (2013.01); *A61M 5/24* (2013.01); *A61M 5/3158* (2013.01); *A61M 5/31501* (2013.01); *A61M 5/31535* (2013.01); *A61M 5/31563* (2013.01); *A61M 2005/14506* (2013.01)

(56) References Cited

U.S. PATENT DOCUMENTS

| | | | |
|---|---|---|---|
| 4,936,833 A | | 6/1990 | Sams |
| 4,973,318 A | * | 11/1990 | Holm et al. ............ A61M 5/24 604/208 |
| 5,026,343 A | | 6/1991 | Holzer |
| 5,042,977 A | | 8/1991 | Bechtold et al. |
| 5,112,317 A | | 5/1992 | Michel |
| 5,226,895 A | | 7/1993 | Harris |
| 5,279,585 A | | 1/1994 | Balkwill |
| 5,295,976 A | | 3/1994 | Harris |
| 5,304,152 A | | 4/1994 | Sams |
| 5,308,340 A | | 5/1994 | Harris |
| 5,320,609 A | | 6/1994 | Haber et al. |
| 5,383,865 A | | 1/1995 | Michel |
| 5,514,097 A | | 5/1996 | Knauer |
| 5,545,147 A | | 8/1996 | Harris |
| 5,584,815 A | | 12/1996 | Pawelka et al. |
| 5,591,136 A | | 1/1997 | Gabriel |
| 5,611,783 A | | 3/1997 | Mikkelsen |
| 5,630,796 A | | 5/1997 | Bellhouse et al. |
| 5,725,508 A | | 3/1998 | Chanoch et al. |
| 5,820,602 A | | 10/1998 | Kovelman et al. |
| 5,957,896 A | | 9/1999 | Bendek et al. |
| 6,059,755 A | | 5/2000 | Michel |
| 6,096,010 A | | 8/2000 | Walters et al. |
| 6,146,361 A | | 11/2000 | DiBiasi et al. |
| 6,200,296 B1 | | 3/2001 | Dibiasi et al. |
| 6,221,046 B1 | | 4/2001 | Burroughs et al. |
| 6,235,004 B1 | | 5/2001 | Steenfeldt-Jensen et al. |
| 6,248,095 B1 | | 6/2001 | Giambattista et al. |
| 6,364,860 B1 | | 4/2002 | Steck et al. |
| 6,423,035 B1 | | 7/2002 | Das et al. |
| 6,582,408 B1 | | 6/2003 | Buch-Rasmussen et al. |
| 6,585,698 B1 | | 7/2003 | Packman et al. |
| 6,623,446 B1 | | 9/2003 | Navelier et al. |
| 6,699,224 B2 | | 3/2004 | Kirchhofer et al. |
| 6,899,698 B2 | | 5/2005 | Sams |
| 7,309,327 B2 | | 12/2007 | Kirchhofer et al. |
| 7,377,912 B2 | | 5/2008 | Graf et al. |
| 2004/0186431 A1 | | 9/2004 | Graf |
| 2004/0186441 A1 | | 9/2004 | Graf |
| 2004/0186442 A1 | | 9/2004 | Graf et al. |
| 2004/0215152 A1 | | 10/2004 | Kirchhofer et al. |
| 2004/0215153 A1 | | 10/2004 | Graf |
| 2007/0270761 A1 | | 11/2007 | Kirchhofer et al. |
| 2007/0270762 A1 | | 11/2007 | Kirchhofer et al. |
| 2007/0276341 A1 | | 11/2007 | Graf et al. |
| 2008/0195051 A1 | | 8/2008 | Graf et al. |
| 2008/0195057 A1 | | 8/2008 | Graf et al. |

FOREIGN PATENT DOCUMENTS

| | | |
|---|---|---|
| DE | 4223958 | 1/1993 |
| DE | 4425763 | 1/1996 |
| DE | 19948988 | 4/2000 |
| DE | 19900792 | 6/2000 |
| EP | 0058536 | 8/1982 |
| EP | 0295075 | 12/1988 |
| EP | 0327910 | 8/1989 |
| EP | 0496141 | 7/1992 |
| EP | 0498737 | 8/1992 |
| EP | 0594349 | 4/1994 |
| EP | 0879610 | 11/1998 |
| EP | 0897728 | 2/1999 |
| EP | 0897729 | 2/1999 |
| EP | 1074273 | 2/2001 |
| EP | 1095668 | 5/2001 |
| EP | 0937476 | 1/2005 |
| WO | 9009202 | 8/1990 |
| WO | 9717095 | 5/1997 |
| WO | 9717096 | 5/1997 |
| WO | 9938554 | 8/1999 |
| WO | 0002606 | 1/2000 |
| WO | 0230495 | 4/2002 |

\* cited by examiner

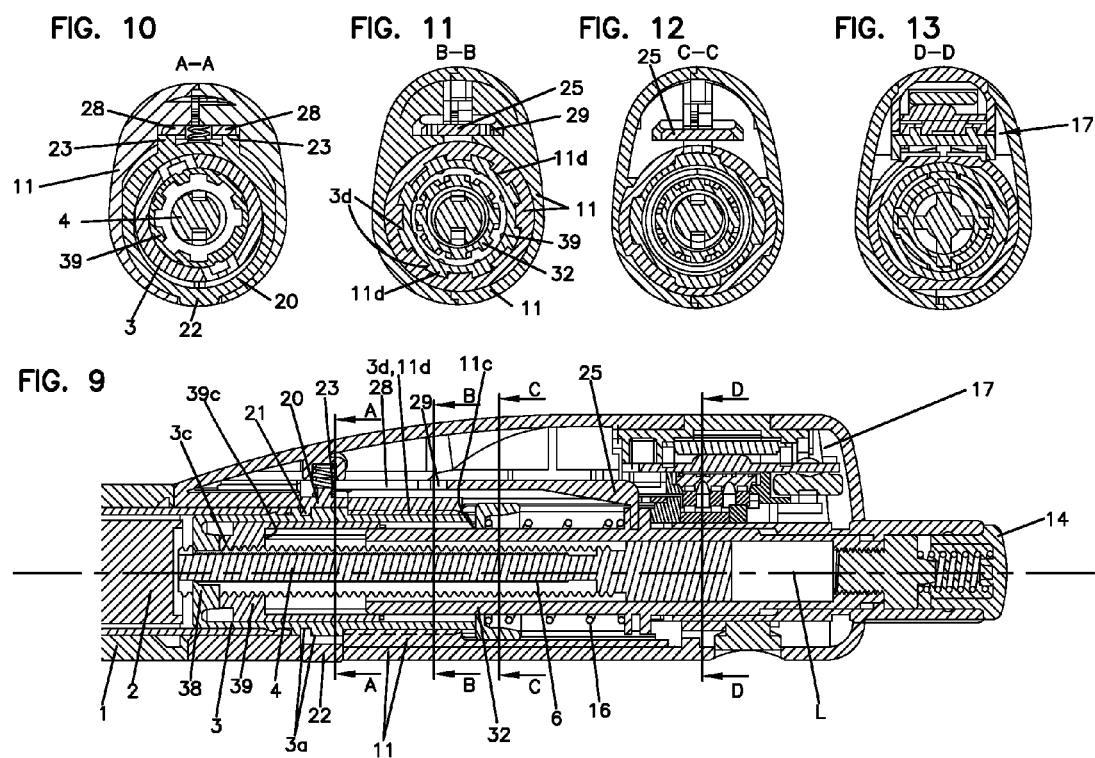

A-A

RESERVOIR MODULE COMPRISING A PISTON ROD

CROSS-REFERENCE TO RELATED APPLICATIONS

This application is a continuation application of U.S. application Ser. No. 11/836,474 filed Aug. 9, 2007, which is a divisional application of U.S. application Ser. No. 10/767,974, filed Jan. 29, 2004, which is a continuation of International Application No. PCT/CH02/00411, filed on Jul. 22, 2002, which claims priority to German Application No. 201 12 501.3, filed on Jul. 30, 2001 and German Application No. 101 63 327.0, filed on Dec. 21, 2001, the contents of all of which are incorporated herein by reference in their entirety.

BACKGROUND

The invention relates to administering devices, including injection devices, and methods of their operation and use. More particularly, it relates to a reservoir module which has an associated piston rod, and a dispensing or administering apparatus comprising such a reservoir module.

In a preferred embodiment, the product dispensing or administering apparatus is an injection apparatus or inhalation apparatus for medical, therapeutic, diagnostic, pharmaceutical or cosmetic applications. One preferred example of injection apparatus is injection pens, in particular semi-disposable pens.

WO 97/17095 describes an injection apparatus consisting of a dosing and activating module and a reservoir module which are detachably connected to each other. The reservoir module is designed as a disposable module, while the dosing and activating module is intended to be re-used—once the reservoir module has been used up or emptied—with a new reservoir module. The reservoir module contains a reservoir for a product to be injected and mounts a piston rod which acts on a piston accommodated in the reservoir to deliver product. The piston rod comprises an outer thread which is in threaded engagement with an inner thread of a dosing setting member. The piston rod is linearly guided, such that when the dosing setting member is rotated, the piston rod is moved towards the piston and a slight distance between a front end of the piston rod and the piston is thus changed. The reservoir module also mounts the dosing setting member and thus comprises the piston rod and the dosing setting member, which are disposed of together with the reservoir as a single module, after the reservoir as been emptied.

An advantage of the design of such semi-disposable injection apparatus is that the parts of the injection apparatus involved in dosing and delivery only have to be configured for delivering the contents of a single reservoir. This reduces the price of these parts. Since, if repeatedly used, such parts would always have to be guided back again to an initial position by the user, they would furthermore be exposed to a risk of damage which should not be underestimated. The reliability of correctly selecting and delivering the dosage need not therefore be less for semi-disposable injection apparatus than for completely re-usable apparatus. Moreover, exchanging a complete reservoir module is simpler than exchanging only a reservoir.

The dosage setting member of the known apparatus is pushed into a rear position, in which the product is dosed, by a pressure spring which is supported by a casing of the reservoir module. By dosing the product, the piston rod is advanced towards the piston relative to the dosage setting member and the casing of the reservoir module. The product is delivered by means of a dosing and activating device which is mounted in a casing of the dosing and activating module and pushes against a rear abutting area of the dosage setting member. The dosing and activating device pushes the dosage setting member, and due to the threaded engagement also the piston rod together with it, in the advancing direction.

SUMMARY

It is an object of the invention to provide a dose administering or dispensing apparatus, in particular injection apparatus, using a reservoir module which has an associated piston rod, while maintaining reliability with respect to correctly selecting and delivering a dose.

It is an object of the invention to further reduce the price of administering or dispensing apparatus, in particular injection apparatus, using a reservoir module which serves as a piston rod mount or carrier, while maintaining reliability with respect to correctly selecting and delivering a product dosage.

The invention relates to product dispensing apparatus, in some embodiments injection apparatus, comprising a reservoir module and a dosing and activating module, which are detachably connected to each other.

In one embodiment, the present invention comprises a dispensing apparatus comprising a reservoir module comprising a front casing section, a block, a first connector, a piston, and a piston rod moveable in and against a dispensing movement and including a return block engageable with the block, wherein engagement between the block and the return block prevents the piston rod from moving against the dispensing movement, a dosing module comprising a rear casing section including a second connector engageable with the first connector to form a detachable connection between the reservoir module and the dosing module, and a dose setting member engageable with the piston rod such that it is moveable together with and in the same direction as the piston rod during the dispensing movement and is moveable relative to the piston rod against the dispensing movement.

In some embodiments, the product dispensing apparatus is preferably already formed by two modules alone, the reservoir module and the dosing module, which carry the operating components or operating mechanisms. The reservoir module comprises a front casing section of the product dispensing apparatus, comprising a reservoir for a product to be delivered, which is preferably fluidic and can be injected, and a first connecting means. A piston is accommodated in the reservoir, such that product is delivered from the reservoir by shifting the piston in an advancing direction. The reservoir module further comprises a piston rod which is held by the front casing section. Lastly, the reservoir module can comprise an injection needle, or a nozzle for needle-free injections.

The reservoir can be formed by a container which is accommodated by the casing. For example, an ampoule can form the reservoir. In principle, however, the reservoir can also be formed by the casing itself, i.e., without interposing a product container. The product to be injected or administered is preferably a liquid for medical, therapeutic, diagnostic, pharmaceutical or cosmetic applications, for example insulin or a growth hormone. In some embodiments, the product dispensing apparatus is preferably an injection apparatus and is preferably employed in applications in which a user self-administers the product him/herself, as is common in diabetes therapy. However, its use in the field of in-patients or out-patients, by trained staff, is not to be excluded. In other applications or uses, in which it is necessary or desirable to dispense a product in doses, the product can be a paste.

The piston rod can be connected fixedly, i.e., permanently, to the piston, by which forming or integrating the piston and piston rod as one piece is also to be understood. In a preferred embodiment, however, the piston and the piston rod are embodied as separate components, and a front end of the piston rod pushes against a rear side of the piston for the purpose of delivering product.

The dosing and activating, or actuating, module comprises a rear casing section of the product dispensing apparatus, comprising a second connecting means which together with the first connecting means forms the detachable connection between the reservoir module and the dosing and activating module. In some embodiments, the front casing section and the rear casing section preferably form the whole casing of the apparatus. The first and second connecting means can, for example, take the form of a rotational connection, in particular a screw connection. In some preferred embodiments, the two casing sections are linearly slid onto each other, wherein the first connecting means and the second connecting means form a linear guide which prevents the two casing sections from rotating relative to each other. Furthermore, they preferably form a latching means together, such that the regions of the casing sections slid over each other cannot simply be pulled apart again.

The dosing and activating module further comprises a dosing and drive element for providing or performing a dosing movement for selecting a product dosage and a delivery movement for delivering the product dosage. Such movements may be performed relative to the connected casing sections.

If the connecting means form a latching means, in some embodiments, the latching means preferably comprises a latching block which only allows the two casing sections to be latched or connected to each other in a front end position of a drive element or the dosing and drive element of the dosing and drive device.

In some embodiments, the product dispensing apparatus comprises a dosage setting member which is moved in the advancing direction by the dosing and drive device during the delivery movement, and which engages with each of the piston rod and at least one of the casing sections such that it can only be moved jointly with the piston rod in the advancing direction and is moved counter to the advancing direction, relative to the piston rod, by the dosing movement of the dosing and drive device. In some embodiments, the engagement with the piston rod is preferably a threaded engagement. In principle, however, the engagement can also be formed differently, for example as a toothed engagement which allows the dosage setting member to move counter to the advancing direction relative to the piston rod, but prevents the dosage setting member from moving in the advancing direction relative to the piston rod. While the dosage setting member can in principle be a component of the dosing and activating module, it is, in some embodiments, a component of or coupled to the reservoir module, i.e., it is preferably already held on the reservoir module before the reservoir module is connected to the dosing and activating module.

In accordance with the invention, the front casing section comprises a blocking means and the piston rod comprises a returning blocking means, which are in blocking engagement with each other, the blocking engagement allowing the piston rod to move in the advancing direction relative to the front casing section, but preventing this counter to the advancing direction. As a desired side effect, the blocking engagement alone can ensure that the piston rod is not moved in the advancing direction relative to the front casing section while the product dosage is being selected. If the piston rod is not yet fixed sufficiently securely for this purpose by the blocking engagement alone, the blocking means also comprises a braking means in order to prevent the piston rod from moving in the advancing direction while the product dosage is being selected, by exerting an additional frictional force.

In the product dispensing apparatus of the invention, as compared to the apparatus of WO 97/17095, a pressure spring is eliminated, which in the known apparatus ensures that the piston rod and the dosage setting member assume their rearmost position during the dosing process. Saving on parts simultaneously means saving on costs. The saving effect is augmented by the fact that the reduction in the number of parts is registered on the side of the reservoir module. Since, in some embodiments, the reservoir module in accordance with the invention is preferably designed as a disposable module, the saving effect makes itself felt every time such a reservoir module is exchanged.

In embodiments in which the dosage setting member participates in the dosing movement of the dosing and drive device, it is preferably ensured—when establishing the coupling between the dosing and drive device and the dosage setting member necessary for this, brought about by connecting the two modules—that a dosing movement of the dosage setting member cannot occur. For this purpose, the dosage setting member and the dosing element or combined dosing and drive element of the dosing and drive device, to be coupled to the dosage setting member, are held with respect to each other in pre-set positions with respect to the dosing movement when connecting the modules. If the dosing movement is a rotational movement about a rotational axis pointing in the direction of the delivery movement, the dosage setting member and the dosing element or dosing and drive element are held with respect to each other in pre-set rotational angular positions, when connecting the modules. If the dosage setting member and the dosing element or dosing and drive element are held by the front casing section and rear casing section, respectively, in a pre-set rotational angular position, then the cited linear guide of the casing sections can advantageously ensure that establishing the coupling does not cause a dosing movement of the dosage setting member. If the casing sections perform a rotational movement relative to each other when the modules are connected, a dosing movement of the dosage setting member is prevented another way.

The product dispensing apparatus can comprise a block which ensures that the reservoir module can only be detached from the dosing and activating module in a foremost position of the piston rod. In order to reliably prevent the reservoir module from being used again, it is necessary in this case to hold the piston rod in its foremost position, such that the user cannot transfer it back to an axial position in which, once the reservoir has been exchanged, product can be delivered again using the same piston rod. In some preferred embodiments, the blocking engagement between the returning blocking means formed on the piston rod and the blocking means of the front casing section hold the piston rod after each individual delivery of a product dosage, such that it is prevented from being transferred to an earlier axial position. If it is further ensured that the piston rod and the reservoir cannot be separated from each other, the reservoir is advantageously prevented from being exchanged in all axial positions of the piston rod. The blocking engagement thus also simultaneously forms a securing engagement in any axial position of the piston rod.

In preferred exemplary embodiments, the returning blocking means is formed by serrated teeth which project from the piston rod and form a row of teeth having a preferably regular separation. The present invention has recognized that the principle of the toothed rack, known in its own right for dosing, can be advantageously employed in a reservoir module designed as a disposable module, in order to lower the costs for the reservoir module and as a result especially also for the product dispensing system as a whole. A row of serrated teeth, comprising teeth tapered in the advancing direction and rear blocking areas, also simultaneously provides, as a by-product in each blocking engagement, the securing engagement which prevents the piston rod from returning.

The securing engagement between the blocking means and the piston rod, which prevents the piston rod from returning, is non-releasable. In this context, non-releasable means that it cannot be released by the user without being destroyed. However, it should not be ruled out that the reservoir module can be reprocessed into a closed cycle and that the blocking engagement can in this case be released, for example by the manufacturer by means of special tools. It is, however, ensured that a user who is using the product dispensing apparatus for self-administering, for example for administering insulin or growth hormones, cannot exchange or re-fill the reservoir.

The dosing and drive device of the present invention may operate manually, semi-automatically or fully automatically. In the first case, both the rotational dosing movement and the translational delivery movement are performed manually. In the second case, either the rotational dosing movement or the translational delivery movement is performed manually and the other movement is performed using motors or by means of another type of force application, for example by means of a spring force, when the user has triggered the corresponding movement using an activating handle or other suitable actuator. In the third case, that of the fully automatic dosing and drive device, the dosing movement and the delivery movement are performed using motors or by means of another force, for example a spring force. In this case, only the dosage is selected manually, for example by means of one or more buttons, and the delivery movement is likewise triggered by the user using a corresponding activating handle of its own. In most embodiments, the administering apparatus in accordance with the invention is equipped with a manual dosing and drive device, which is then referred to as a dosing and activating device. Thus, whenever a dosing and activating device is mentioned, it is therefore the manual embodiment which is being referred to. Where a dosing and drive device is mentioned, this is not intended to restrict the invention with respect to being manual, semi-automatic or fully automatic, but rather to comprise each of these embodiments. The term "dosing and activating module" is, however, used in connection with all the embodiments of the dosing and drive device.

The dosing and drive device can separately comprise a dosing element which performs the dosing movement and a drive element which performs the delivery movement. In some preferred embodiments, however, the dosing movement and the delivery movement are performed by the same body of the dosing and drive device which is therefore also referred to in the following as a dosing and drive element or dosing and activating element.

The present invention may be used to deliver or administer any suitable substance or product, including a fluid or a liquid such as those having a medical, therapeutic, diagnostic, pharmaceutical or cosmetic application. The product can for example be insulin, a growth hormone, or a thin or thick, pulpy food. The administering apparatus may be employed in applications in which a user self-administers to him/herself, as is common in diabetes therapy, however, its use in the field of in-patients or out-patients, by trained staff is not to be excluded.

In the case of an injection apparatus, the product can be administered by means of an injection cannula or a nozzle for needle-free injections. The product can be injected or infused subcutaneously or venously, or also intramuscularly. When administered by inhalation, the selected product dosage can be delivered from the reservoir into a chamber of the inhalation apparatus and vaporized for inhalation by means of a vaporizing means. Furthermore, oral ingestion is conceivable, or administering via the esophagus, to name but a few administering examples.

In some embodiments, the administering apparatus is preferably semi-disposable. In this case, the front casing section is a support for a reservoir module which is disposed of or recycled once the reservoir has been emptied, and the rear casing section is a support for a dosing and activating module which can be repeatedly used in conjunction with a new reservoir module. Since the reservoir module can also be treated separately as a disposable module, it is also a separate subject of the invention. The dosing and activating module can also be also a separate subject of the invention. Equally, a system consisting of an administering apparatus and at least one reservoir module, which can replace the reservoir module of the apparatus once it has been used, forms a subject of the invention. The duplex design of the administering apparatus, divided into a portion provided for use only once and a portion provided for repeated use (semi-disposable), is advantageous for injection pens in particular, but also for example for inhalation apparatus or apparatus for orally ingesting a product or for artificial feeding.

BRIEF DESCRIPTION OF THE DRAWINGS

FIG. 9 depicts a second exemplary embodiment of an injection apparatus;

FIG. 10 depicts the cross-section A-A of FIG. 9;

FIG. 11 is the cross-section B-B of FIG. 9;

FIG. 12 is the cross-section C-C of FIG. 9;

FIG. 13 is the cross-section D-D of FIG. 9;

DETAILED DESCRIPTION

Figure 1:
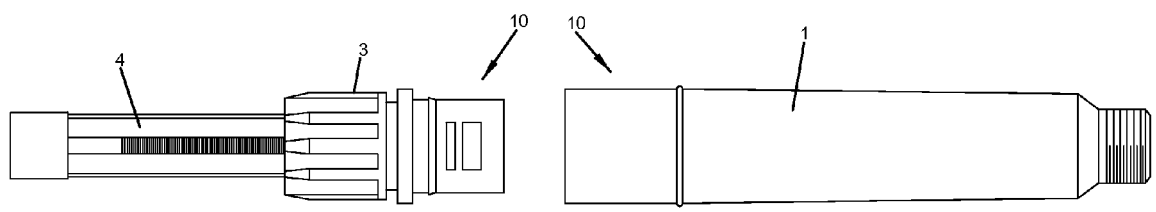
FIG. 1 depicts two portions of a reservoir module in accordance with a first exemplary embodiment.
Figure 2:
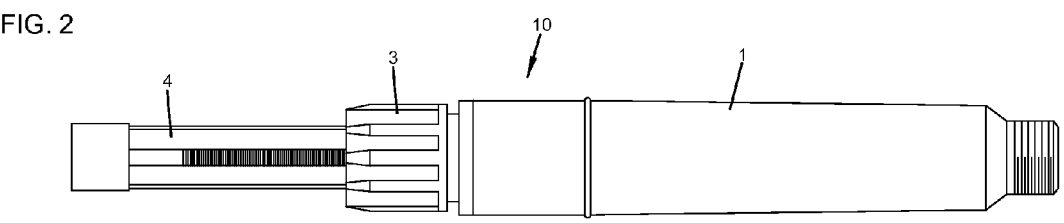
FIG. 2 depicts the reservoir module obtained from the two portions of FIG. 1.

FIG. 1 shows a view of a reservoir part 1 and a mechanism holder 3, which are connected to each other to form the reservoir module 10 shown in FIG. 2.

In FIGS. 1 and 2, a piston rod can be seen which protrudes, on an end of the mechanism holder 3 facing away from the reservoir part 1, into the mechanism holder 3 and is mounted by the mechanism holder 3 such that it can shift in an advancing direction pointing in the longitudinal axis L of the piston rod 4, towards a front end of the reservoir part 1 facing away from the mechanism holder 3. The reservoir part 1 is substantially a hollow cylinder which has a circular cross-section and comprises a connecting region at its front end for connecting to a needle holder for an injection needle. The reservoir part 1 serves to accommodate a reservoir container which in the embodiment is formed by an ampoule 2 which can be seen in the longitudinal section in FIG. 3. An outlet at the front end of the ampoule 2 is sealed fluid-tight by a membrane. When the needle holder is fastened to the front end of the reservoir part 1, a rear portion of the injection needle pierces the membrane, such that a fluid connection between the tip of the hollow injection needle and the reservoir 2 is established.

Figure 3:
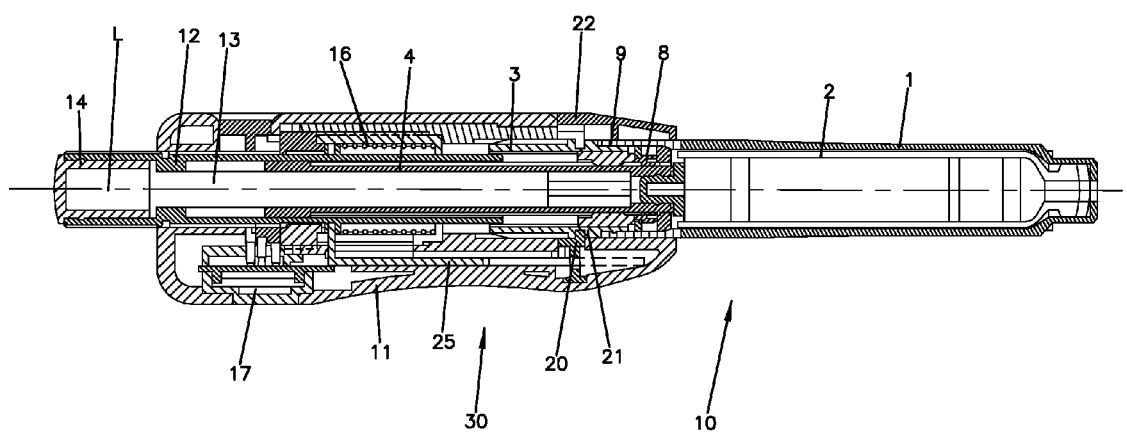
FIG. 3 depicts an injection apparatus comprising the reservoir module of FIG. 2, in accordance with the first exemplary embodiment, in a longitudinal section.

FIG. 3 shows the injection apparatus in its entirety, in a longitudinal section. A piston is accommodated in the ampoule 2 such that it can shift in the advancing direction towards the outlet formed at the front end of the ampoule 2. Shifting the piston in the advancing direction displaces product out of the ampoule 2 and delivers it through the outlet and the injection needle.

The piston is advanced by the piston rod 4 which pushes against the piston via its front end and thus moves the piston in the advancing direction when advanced itself. The piston rod 4 is held by the mechanism holder 3 such that it can be moved in the advancing direction once a certain resistance has been overcome, but not counter to the advancing direction. The piston rod 4 is prevented from moving backwards, counter to the advancing direction, by a blocking means 8. The blocking means 8 is axially fixed by the mechanism holder 3, i.e., it is held in the mechanism holder 3 such that it cannot be moved in and counter to the advancing direction. It is, however, mounted by the mechanism holder 3 such that it can be rotated about the longitudinal axis L. The blocking means 8 also generates the resistance which has to be overcome in order to move forwards.

Figure 5A:
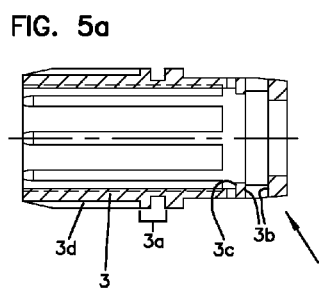
FIGS. 5a-5c depict a mechanism holder of the reservoir module, in a longitudinal section and two views.
Figure 5C:
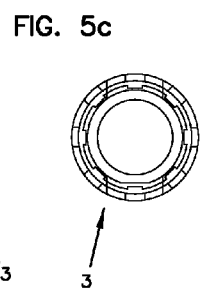
Figure 6A:
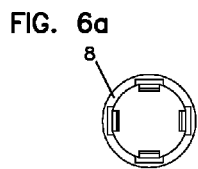
FIGS. 6a-6d depict a blocking means for a piston rod, mounted by the mechanism holder.
Figure 6C:
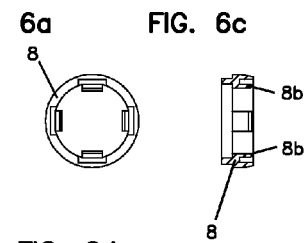
Figure 6B:
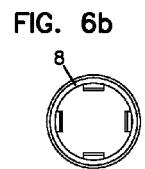
Figure 6D:
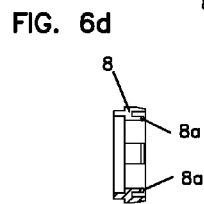
Figure 5B:
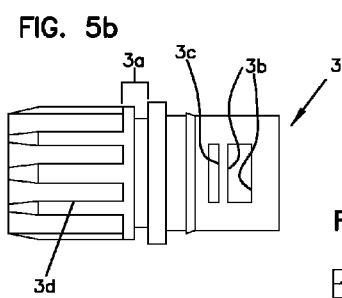

The blocking means 8 is shown on its own in FIGS. 6a-6d. It is formed by a one-part annular element which, rotatable about the longitudinal axis L, abuts the mechanism holder 3 between two facing, spaced collars 3b which protrude radially inwards from an inner surface of the mechanism holder 3. The collars 3b form a fixing means for axially fixing the blocking means 8. How the blocking means 8 is mounted in the mechanism holder 3 is most clearly seen from the representation of the mechanism holder 3 in FIGS. 5a-5c.

Furthermore, a dosage setting member 9 is accommodated in the mechanism holder 3. The dosage setting member 9 is formed as a threaded nut and is in threaded engagement with an outer thread of the piston rod 4. The dosage setting member 9 is secured against rotating by the mechanism holder 3, but is guided such that it can move axially and linearly in and counter to the advancing direction. The piston rod 4 and the dosage setting member 9 form a spindle drive for selecting the product dosage to be administered.

The ampoule holder 1 and the mechanism holder 3 are connected to each other, secured against rotating and shifting, and together form the reservoir module 10 of the injection apparatus, said reservoir module 10 comprising the piston rod 4 held by the mechanism holder 3 by means of the blocking means 8, and the dosage setting member 9. The ampoule holder 1 and the mechanism holder 3 together form a front casing section 1' of the injection apparatus. A rear casing section 11 is connected to said front casing section 1' in a positive lock. The rear casing section 11 forms the support for a dosing and activating element 12 and, together with the dosing and activating element 12 and parts of a latching means and other parts, forms a dosing and activating module 30 of the injection apparatus.

Except for the dosage setting member 9, the piston rod 4 and the blocking means 8, a dosing and activating device comprises the other components for selecting the product dosage and activating the injection apparatus. In particular, it comprises the dosing and activating element 12. The dosing and activating device further comprises a counting and indicating means 17 for counting and optically indicating the selected product dosage. Not least, the counting and indicating means 17 makes the dosing and activating module 30 a high-grade and therefore expensive part of the injection apparatus. While the comparatively inexpensive reservoir module 10 is designed as a disposable module, the dosing and activating module 30 is intended for repeated use, with a series of new reservoir modules 10.

For selecting the product dosage or dose, i.e., for dosing, the dosing and activating element 12 can be rotated about the longitudinal axis L and is furthermore mounted by the rear casing section 11 such that it can linearly shift along the longitudinal axis L, in and counter to the advancing direction. The dosing and activating element 12 is hollow cylindrical and surrounds the piston rod 4 via a front section. A rear section of the dosing and activating element 12 protrudes out beyond a rear end of the casing section 11. A rod-shaped dosing slaving means 13 is inserted into the dosing and activating element 12 from the rear, as far as a collar of the dosing and activating element 12 protruding radially inwards. Furthermore, at the rear end, a closure 14 is inserted into the dosing and activating element 12, as far as the dosing slaving means 13. The dosing slaving means 13 is axially fixed relative to the dosing and activating element 12 between the radially protruding collar of the dosing and activating element 12 and the closure 14. The dosing slaving means 13 is also connected, secured against rotating, to the dosing and activating element 12. For the purpose of dosing, the dosing slaving means 13 protrudes into the hollow piston rod 4 from the rear. The piston rod 4 comprises a connecting section 4a (FIG. 4) which engages with the dosing slaving means 13 such that the piston rod 4 and the dosing slaving means 13 and therefore also the dosing and activating element 12 cannot be rotated relative to each other about the common longitudinal axis L, but can be moved relative to each other along the longitudinal axis L, in and counter to the advancing direction. For this purpose, the connecting section 4a is formed as a linear guide for the dosing slaving means 13.

Figure 4:
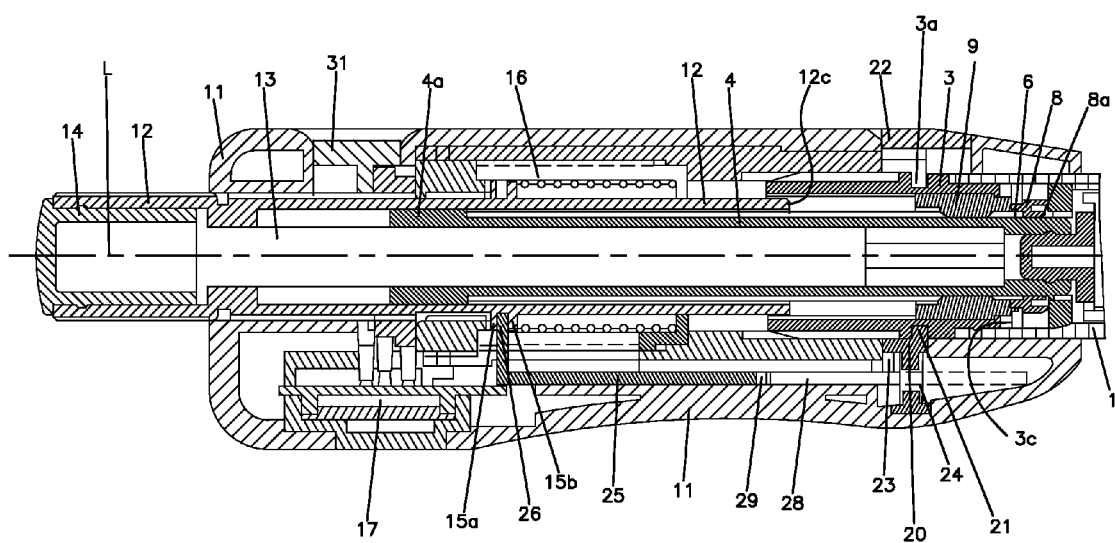
FIG. 4 depicts a portion of the injection apparatus of FIG. 3.

A restoring means 16 elastically tenses the dosing and activating element 12 counter to the advancing direction, into the initial position shown in FIGS. 3 and 4. In the initial position, the product can be dosed by rotating the dosing and activating element 12 about the longitudinal axis L. Then, from the initial position, the selected product dosage can be delivered by axially shifting the dosing and activating element 12. The restoring means 16 is formed by a spiral spring acting as a pressure spring, which is accommodated in an annular gap around the dosing and activating element 12 and axially supported between a collar of the casing section 11 protruding radially inwards and a collar of the dosing and activating element 12 facing opposite and protruding radially outwards.

The blocking means 8 fulfils a double function. On the one hand, it ensures via its blocking elements 8a that the piston rod 4 cannot be moved back, counter to the advancing direction, relative to the mechanism holder 3 and therefore in particular relative to the piston accommodated in the ampoule 2. In its double function as a brake, the blocking means 8 furthermore prevents the piston rod 4 from moving forwards during the dosing process in which the dosage setting member 9 is moved axially, counter to the advancing direction, towards the dosing and activating element 12.

In the initial position shown in FIGS. 3 and 4, before dosing, the dosage setting member 9 abuts against a delivery stopper 3c (FIGS. 5a-5c) formed by the mechanism holder 3, in the advancing direction. The piston rod 4 is in permanent touching contact with the piston. For the purpose of dosing, the dosage setting member 9 is moved away from the delivery stopper 3c towards the dosing and activating element 12 by the threaded engagement with the piston rod 4 and the linear guide from the mechanism holder 3. This reduces a slight distance between a rear stopper area of the dosage setting member 9 and a front stopper area of the dosing and activating element 12, but on the other hand increases the slight distance between a front stopper area of the dosage setting member 9 and the delivery stopper 3c. The latter distance between the delivery stopper 3c and the dosage setting member 9 is the path length by which the dosage setting member 9 and—due to the threaded engagement—also the piston rod 4 are moved in the advancing direction in the course of the delivery movement of the dosing and activating element 12. The delivery stopper 3c forms a front translational stopper. During the delivery movement, the piston rod 4 pushes via its front end, which is formed by a plunger body connected to the piston rod 4 such that it cannot move in or counter to the advancing direction, against the piston and pushes the piston forwards in the advancing direction towards the outlet of the ampoule 2. The longitudinal axis L forms the rotational and translational axis of the movements which are performed for the purpose of dosing and delivering the product.

The distance which the dosage setting member 9 and the dosing and activating element 12 exhibit between each other during the dosing process when the dosage setting member 9 abuts against the delivery stopper 3c corresponds to the maximum product dosage which can be selected and delivered in the course of a delivery. The stroke movement of the dosing and activating element 12 is of equal length for each delivery. Dosing merely sets the distance between the dosage setting member 9 and the delivery stopper 3c and therefore the path length which can be jointly traveled by the dosing and activating element 12 and the dosage setting member 9 in the course of delivery.

Figure 7A:
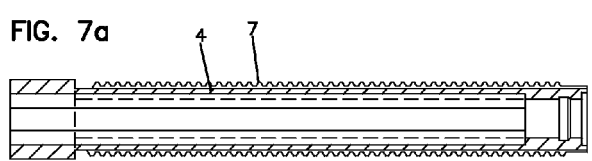
FIGS. 7a-7b depict a piston rod in a longitudinal section and a front view.
Figure 7B:
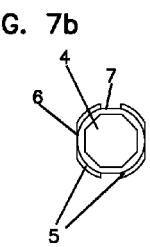

The braking function of the blocking means 8 and the braking engagement which exists between the piston rod 4 and the blocking means 8 for this purpose are clear from an overview of FIGS. 6 and 7. On the one hand, the blocking means 8 comprises two braking elements 8b for the braking engagement, which are each formed by an elastically flexing catch, like the blocking elements 8a before them. In the depicted embodiment, the blocking means 8 is formed by a single annular element from which four elastic catches axially project on an abutting side. The catches are arranged in a uniform distribution over the circumference of the annular element. Two mutually opposing catches form the blocking elements 8a and the other two catches, likewise arranged mutually opposing, form the braking elements 8b.

The piston rod 4 accordingly comprises two returning blocking means 6, which are formed on the outer surface on opposing sides and extend in the longitudinal direction of the piston rod 4, and two advancing braking means 7, which likewise extend in the longitudinal direction of the piston rod 4 on mutually opposing sides. The thread of the piston rod 4 for the threaded engagement with the dosage setting member 9 is formed by four remaining threaded sections 5 which extend over almost the entire length of the piston rod 4. The returning blocking means 6 and the advancing braking means 7 are each formed by a row of teeth. However, while the teeth of the returning blocking means 6 are formed as serrated teeth, narrowing in the advancing direction and comprising blocking areas pointing backwards and extending transverse to the advancing direction, the two rows of teeth which form the advancing braking means 7 do not comprise blocking areas pointing forwards having a comparable blocking effect. The teeth of the advancing braking means 7 each exhibit a "softer" tooth profile as compared to the returning blocking means 6. For the braking engagement between the blocking means 8 and the advancing braking means 7 of the piston rod 4 is not intended to prevent the piston rod 4 from being advanced, but merely to make it more difficult, in order to ensure that the piston rod 4 is not moved in the advancing direction during dosing. The front sides of the teeth of the advancing braking means 7 and the rear sides of the braking elements 8b, which touch the front sides of the teeth of the advancing braking means 7, are shaped such that a threshold force which is not reached during dosing has to be overcome in order to overcome the braking engagement. This threshold force is larger than the force required to move the teeth of the returning blocking means 6 over the blocking elements 8a in the advancing direction. The threshold force is preferably at least twice as large as the initial frictional force between the returning blocking means 6 and the blocking elements 8a. The frictional force between the latter also only increases gradually between two consecutive blocking engagements in the course of the advancing movement. The threshold force of the braking engagement, by contrast, has to be applied from one blocking engagement to the next, immediately at the beginning of the advancing movement, in each blocking engagement. The threshold force should not, however, be so large that it distracts the user during delivery.

An undesired advancing movement by the piston rod as a response to the movement by the dosage setting member 9 when selecting the dosage can in principle also be prevented by the blocking engagement of the blocking means 8 alone. However, such a movement is more reliably prevented because of the braking engagement than by the blocking engagement alone.

The connection between the reservoir module 10 and the dosing and activating module 30 is a positive lock. On the one hand, a latching engagement exists between the mechanism holder 3 and the casing section 11 which prevents relative movement in the axial direction. Beyond the latching engagement, the front casing section 1' and the rear casing section 11 are guided axially and linearly directly onto each other, in order to prevent relative rotating when connected or connected. The axial guides 3d of the mechanism holder 3, which together with one or more corresponding engagement elements of the rear casing section 11 form the linear guide, can be clearly seen in FIGS. 5a-5c. The axial guides 3d are formed by guide areas on guide ribs; they could also be formed by guide areas in axially extending recesses. In this way, axial guide channels are obtained. The guide ribs are axially tapered, such that insertion funnels leading into the guide channels are formed for the one or more engagement elements of the rear casing section 11. In order to even better center the casing sections 1, 3 and 11 at the beginning of connecting, the guide ribs are also tapered in the radial direction. The one or more engagement elements of the rear casing section 11 is or are preferably formed like the axial sections 3*d* on the surface counter area, i.e., the inner surface area of the rear casing section 11.

The latching engagement exists between a first, female latching element 3*a* of the mechanism holder 3 (FIGS. 5*a*-5*c*) and a latching ring 20 which is connected to the rear casing section 11 such that it can move radially but not axially. The latching ring 20 forms a second, male latching element 21 which radially engages directly with the first latching element 3*a*. A lock/latch connection exists between the first latching element 3*a* and the second latching element 21 which prevents the reservoir module 10 and the dosing and activating module 30 from moving axially relative to each other.

FIGS. 3 and 4 show the latching element 21 in latching engagement with the latching element 3*a*. The latching element 3*a* is formed by an annular stay and a groove which runs around the outer surface of the mechanism holder 3. The annular stay forms a rear side wall of the groove. The second latching element 21 is formed by a cam which protrudes radially inwards from the inner surface of the latching ring 20 and which in the latching engagement is pushed radially inwards over an inner surface area of the rear casing section 11, protruding into the accommodating latching element 3*a*, by a restoring means 24. The latching ring 20 is supported in its entirety in the radial direction on an inner surface area formed by the rear casing section 11, by means of the restoring means 24, such that the restoring means 24 pushes against the outer surface of the latching ring 20 roughly in a radial extension of the latching element 21. The latching ring 20 surrounds the mechanism holder 3 and can be moved in its entirety radially back and forth against the restoring force of the restoring means 24, such that the second latching element 21 can be moved in and out of latching engagement with the first latching element 3*a*. The rear casing section 11 forms a tight sliding guide for the radial movement of the latching ring 20. On its side radially opposite the latching element 21, the latching ring 20 forms an unlatching button 22 for the user. In order to radially guide the restoring means 24 formed as a pressure spring, a guide cam projects radially from the outer surface area of the latching ring 20 facing away from the latching element 21.

Two blocking cams 23, which press radially outwards against a latching block 25, furthermore project from the outer surface area of the latching ring 20, in the circumferential direction on both sides of said guide cam and axially behind the guide cam. Since the blocking cams 23 abut against the latching block 25, a radial movement of the latching element 21—which could result in the latching engagement being released—is prevented. The latching engagement between the latching elements 3*a* and 21 is thus secured by the latching block 25. The latching engagement is secured in every position of the dosing and activating element 12, except for a releasing position which the dosing and activating element 12 assumes at the end of its delivery movement. The releasing position therefore coincides with the foremost shifting position which the dosing and activating element 12 assumes when it abuts the dosage setting member 9 in the course of its delivery movement and the dosage setting member 9 for its part abuts against the delivery stopper 3*c* of the mechanism holder 3. Providing the dosing and activating module 30 is not yet connected to the reservoir module, a mechanical stopper for the dosing and activating element 12 is formed by a stopper element 31 of the dosing and activating device. A reset holder ring which serves to reset the indicator 17 forms the stopper element 31. The dosing and activating element 12 abutting against said stopper element 31 defines the releasing position of the dosing and activating element 12 in this case, the releasing position defined by the stopper element 31 corresponding to that defined by the dosage setting member 9 abutting the delivery stopper 3*c*.

Figure 8A:
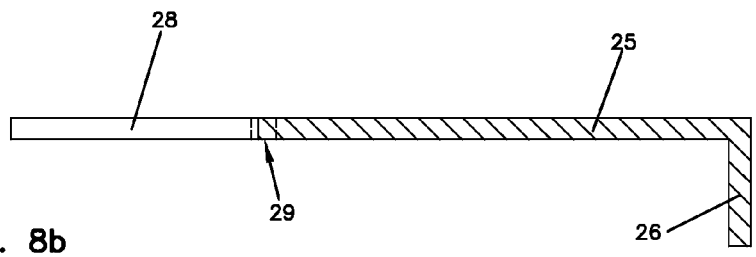
FIGS. 8a-8c depict a latching block in a longitudinal section, a view and a top view.
Figure 8C:
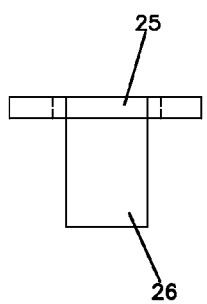
Figure 8B:
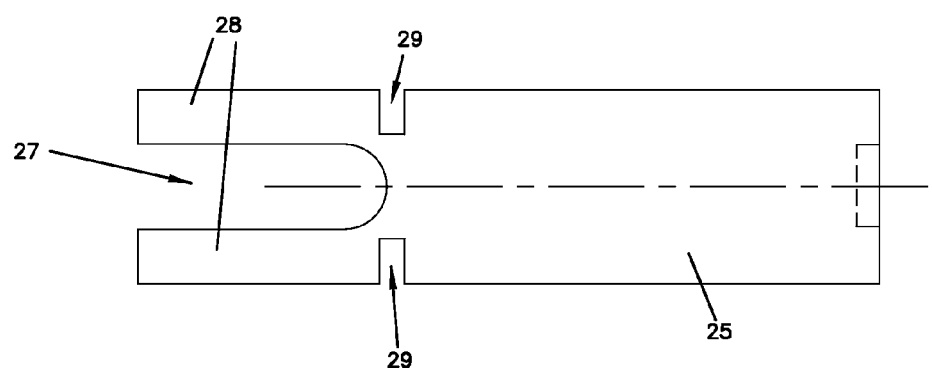

FIGS. 8*a*-8*c* shows the latching block 25. In the exemplary embodiment, it is formed as one piece by a blocking slider. The latching block 25 comprises a plate-shaped main body which extends axially when assembled, as for example shown in FIG. 4. At one end, a stay 26 projects at right angles from the main body. When assembled, the stay 26 extends radially as far as the dosing and activating element 12. The stay 26 serves to fasten the latching block 25 to the dosing and activating element 12 which for this purpose comprises two annular stays formed axially spaced on an outer surface area, which form the slaving means 15*a* and 15*b*. The front slaving means 15*a* simultaneously forms the support collar for the restoring means 16. In the annular space formed between the slaving means 15*a* and 15*b*, the latching block 25 protrudes in via its stay 26 and is tightly enclosed axially on both sides by the two slaving means 15*a* and 15*b*.

At a front end facing away from the stay 26, the main body of the latching block 25 is provided with an axial recess 27 which is open towards the front end of the latching block 25. In this way, blocking tongues 28 extending axially on both sides of the recess 27 are formed. The blocking cams 23 of the latching ring 20 are arranged such that each of said blocking cams 23 pushes against one of the blocking tongues 28, providing the dosing and activating element 12 does not assume the releasing position. When the latching block 25 moves axially, the restoring means 24 for the latching element 21 extends through the axial recess 27.

Indentation recesses 29 are furthermore formed in the main body of the latching block 25, and define the releasing position of the dosing and activating element 12. One indentation recess 29 is provided for each of the blocking cams 23. The position of the indentation recesses 29 is selected such that they only overlap the blocking cams 23, and thus allow the blocking cams 23 to be inserted, when the dosing and activating element 12 has been advanced into its releasing position.

It is clear that in the arrangement specifically selected in the exemplary embodiment, a single blocking cam 23 could also be provided and the latching block 25 accordingly comprise only one indentation recess 29 and possibly also only one blocking tongue 28. Furthermore, the latching block could in principle be produced together with the dosing and activating element 12 as one piece. Forming it as a separate part, however, offers advantages with regard to production, assembly and the dosing and activating element 12 cooperating with the piston rod 4. With respect to the installation length of the latching block 25, it should also be pointed out that the latching block 25 is supported, on its outer side facing away from the latching element 21, on an inner surface area of the casing 11. In this way, the stability of securing the latching engagement is increased. The casing 11 preferably forms an axial guide for the latching block 25.

The functionality of the injection apparatus is described in the following, wherein it is assumed that a new reservoir module 10 and a dosing and activating module 30 which has already been used at least once are assembled and a product is then delivered for the first time.

The dosing and activating module 30 and the new reservoir module 10 are aligned axially with respect to each other, such that their two longitudinal axes are flush with each other. The reservoir module 10 is then inserted via its rear end into the casing 11, which is open to the front, of the dosing and activating module 30.

This centers the casing section 1' and the casing section 11 on the tapered ends of the guide ribs 3d of the mechanism holder 3. While being slid on, the two casing sections are guided axially and linearly onto each other in a rotational angular position pre-set by the linear guide, until the casing sections 1' and 11 assume a connecting end position in which the latching engagement of the latching elements 3a and 21 can be established or can be set by itself.

The dosing and activating element 12 is locked in pre-set rotational angular positions relative to the rear casing section 11. The linear guide of the casing sections 1' and 11 and the rotational angular locking positions of the dosing and activating element 12 are adjusted to each other such that the engagement, secured against rotating, between the dosing and activating element 12 and the piston rod 4 is established in every locking position of the dosing and activating element 12 and every rotational angular position in which the casing sections 1' and 11 are linearly guided onto each other.

If the dosing and activating element 12 is situated in an axial position relative to the casing section 11 which is behind the releasing position, the latching element 21 is held in its radially innermost position by the latching block 25. In this position of the latching element 21, the dosing and activating module 30 and the reservoir module 10 cannot be slid onto each other up to the connecting end position and therefore also cannot be connected to each other, since the annular stay formed on the outer surface of the mechanism holder 3, which forms a part of the first latching element 3a, comes to rest abutting against the second latching element 21 first.

The annular stay can be reduced to a short radial protrusion in the tangential direction, if it is ensured that the casing sections 1' and 11 can only be assembled in the rotational angular position in which such a protrusion and the second latching element 21 come to rest in an axial flush. The annular stay or radial protrusion could also form the first latching element 3a alone, since the essential function of the first latching element 3a is to allow the connection between the reservoir module 10 and the dosing and activating module 30 to be established only when the dosing and activating element 12 assumes its releasing position. If this condition is fulfilled, then the dosing and activating element 12 would ensure, when the connection between the reservoir module 10 and the dosing and activating module 30 is established, that the dosage setting member 9 is situated in its dosing zero position in which it abuts the delivery stopper 3c of the mechanism holder 3.

In order to fulfill the condition described above, the user pushes the dosing and activating element 12 axially forwards relative to the rear casing section 11 as far as the releasing position. In this relative position between the rear casing section 11 and the dosing and activating element 12, the blocking cams 23 can be moved into the indentation recesses 29 of the latching block 25. The user therefore not only pushes the dosing and activating element 12 at least as far as the releasing position, but simultaneously also pushes the second latching element 21 out of latching engagement by means of the unlatching button 22. The reservoir module 10 can then be moved axially over the annular stay of the first latching element 3a and inserted further into the rear casing section 11.

The user can let go of the unlatching button 22. As soon as the second latching element 21 overlaps the first latching element 3a, it snaps into the accommodating latching element 3a due to the force of the restoring means 24, such that the latching engagement is established. The reservoir module 10 and the dosing and activating module 30 are then connected to each other in a defined way with respect to the position of the dosage setting member 9 and the piston rod 4. If the dosage setting member 9 still exhibited a slight distance from the delivery stopper 3c before the latching engagement is established, this distance is eliminated due to the action of the dosing and activating element 12, required to establish the connection. A resultant delivery of product can be accepted and even desired, for the purpose of priming the injection needle. This preferably resets the counting and indicating means 17 to zero.

In the defined initial state brought about in this way, the user can dose the product. The product is dosed by rotating the dosing and activating element 12 about the longitudinal axis L and relative to the casing section 11. Since the dosing slaving means 13 is connected to the dosing and activating element 12, secured against rotating, and for its part engages with the piston rod 4, secured against rotating, the dosing and activating element 12 slaves the piston rod 4 during its rotational dosing movement. Due to the threaded engagement between the piston rod 4 and the dosage setting member 9 and the linear guide of the dosage setting member 9 by the mechanism holder 3, the dosage setting member 9 performs an axial, translational dosing movement, pre-set by the thread pitch of the reciprocal threaded engagement, towards the dosing and activating element 12. The dosing and activating element 12 forms a rear translational stopper 12c which limits the translational dosing movement of the dosage setting member 9 and thus defines the maximum delivery stroke which may be set.

The counting and indicating means 17 counts the dosage units corresponding to the rotational angular position of the dosing and activating element 12 and indicates it optically.

Once the desired product dosage has been selected, the dosing process is completed. The selected product dosage is delivered by means of the delivery movement, pointing in the advancing direction of the piston, of the dosing and activating element 12. In the course of its delivery movement, the dosing and activating element 12 abuts against the dosage setting member 9 and slaves it. When the dosage setting member 9 abuts against the delivery stopper 3c of the mechanism holder 3 in the course of the delivery movement, the delivery movements of the dosing and activating element 12 and the delivery of product are completed. Once the user lets go of the dosing and activating element 12, it is preferably moved counter to the advancing direction, back into a new initial position for dosing and delivering the product again, by the restoring means 16. The counting and indicating means 17 is preferably coupled to the dosing and activating element 12 such that it has in the meantime been reset back to zero. It possibly possesses means for counting and indicating the total product amount already delivered and thus the residue product amount remaining in the ampoule 2.

In order to detach the reservoir module 10 from the dosing and activating module 30, the dosing and activating element 12 is advanced as far as the releasing position, i.e., until it abuts against the dosage setting member 9. in this position, the user can release the latching engagement again by pushing onto the unlatching button 22, and separate the reservoir module 10 from the dosing and activating module 30.

FIGS. 9 to 13 shows a longitudinal section and four cross-sections of a second exemplary embodiment of an injection apparatus. The injection apparatus of the second embodiment is identical to that of the first embodiment with respect to the latch and latching block 25, such that reference is made in this regard to the description of the first embodiment. In particular, the latching block 25 of the second embodiment is identical to that of the first embodiment with respect to all its functional details. The same applies to the latching elements 3a and 21.

The latching ring 20 and the position of the blocking cams 23 relative to the latching element 21 and relative to the latching block 25 in the initial state of the apparatus can be seen particularly clearly in the cross-sections of FIGS. 10, 11 and 12, to which reference is made in this regard, also as representative for the first embodiment.

The injection apparatus of the second embodiment differs from the first embodiment in the engagement and the progression of movement of the components involved in dosing. Furthermore, the mechanism holder fulfils, in addition to the functions of the mechanism holder of the first embodiment, the function of positioning the dosage setting member in discrete rotational angular positions which may be changed relative to the mechanism holder for the purpose of dosing. The blocking means of the second embodiment, by contrast, is embodied more simply than that of the first embodiment. Primarily, only the differences as compared to the first embodiment will be described in the following, wherein for components which are identical in their basic function to the components of the same name in the first embodiment but differ in details, numbers in the thirties with the same end digit, or exactly the same reference numerals as in the first embodiment, as used. Where no statements are made regarding the second embodiment, the corresponding statements regarding the first embodiment shall apply.

In the second embodiment, the dosing and activating element 32, which can be axially and linearly moved relative to the rear casing section 11 and rotated about the longitudinal axis L, is connected to the dosage setting member 39, secured against rotating. The dosing and activating element 32 and the dosage setting member 39 can be moved in and counter to the advancing direction, relative to each other and relative to casing sections 1' and 11. The piston rod 4 is held by a mechanism holder 3, secured against rotating. In cooperation with blocking elements of the blocking means 38, formed on the mechanism holder 3 as one piece, the returning blocking means 6, which is functionally identical to the first embodiment, prevents the piston rod 4 from moving counter to the advancing direction, but allows it to move in the advancing direction. The blocking elements simultaneously form the returning block and the rotational block for the piston rod 4. Furthermore, as previously in the first embodiment, the dosing and activating element 32 forms a sliding guide for the piston rod 4.

During dosing, the dosing and activating element 32 performs the same rotational dosing movement as the dosing and activating element 12 of the first embodiment. However, since the engagement is secured against rotating, the dosage setting member 39 is slaved during the rotational dosing movement. The threaded engagement between the piston rod 4 and the dosage setting member 39 is again comparable to that of the first embodiment, such that due to the rotational dosing movement and the threaded engagement with the piston rod 4, a stopper 39c formed by the dosage setting member 39 is moved, in the course of dosing, counter to the advancing direction, towards a front end of the dosing and activating element 32. As opposed to the first embodiment, the dosage setting member 39 thus completes a rotational dosing movement and a translational dosing movement relative to the front casing section during dosing, while the piston rod 4 remains stationary. Once dosing has been completed, the delivery movement of the dosing and activating element 32 advances the piston rod 4 by the path length which corresponds to the slight distance between a stopper area of the dosage setting member 39 and the delivery stopper 3c of the mechanism holder 3, set by the dosing.

The translational dosing movement of the dosage setting member 39 is limited counter to the advancing direction by a rear translational stopper 11c which is formed directly by the rear casing section 11 itself. In the second embodiment, too, the rotational and translational axis of the components involved in dosing and delivering the product forms the longitudinal axis L.

As in the first embodiment, the front casing section 1' forms a sliding guide for the dosage setting member 39. In order to form the sliding guide, an inner surface area of the mechanism holder 3 and an outer surface area of the dosage setting member 39 are in sliding contact with each other. The dosing and activating element 32 engages with an inner surface area of the dosage setting member 39, to form the connection, secured against rotating, between the dosage setting member 39 and the dosing and activating element 32.

In the second embodiment, the piston rod 4 comprises no braking means of its own beyond the returning blocking means 6. Rather, the front sides of the serrated teeth of the returning blocking means 6 also form the braking means on their own. The piston rod 4 of the second embodiment can, however, be replaced by the piston rod 4 of the first embodiment. Accordingly, the mechanism holder 3 of the second embodiment would in this case also have to form at least one braking element, preferably both braking elements, of the first embodiment.

Figure 14:
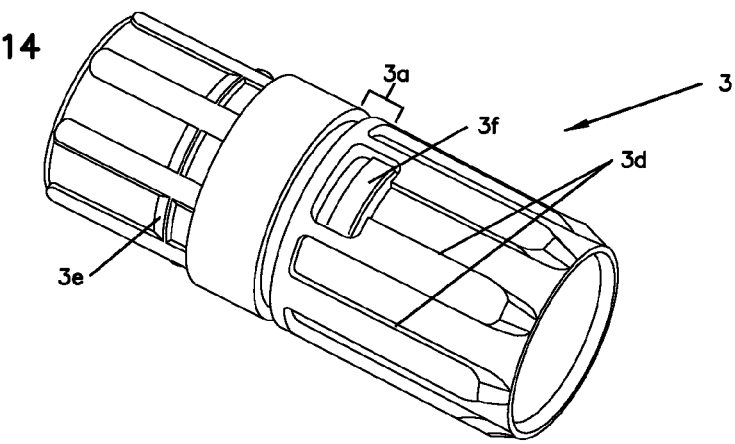
FIG. 14 depicts the mechanism holder of the second embodiment, in a perspective representation.
Figure 16:
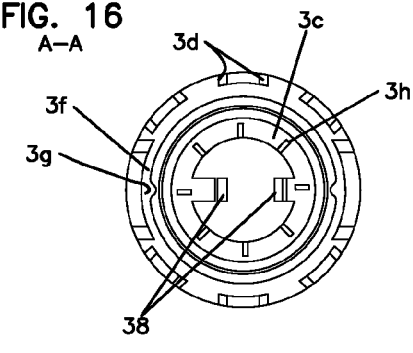
FIG. 16 is the cross-section A-A of FIG. 15.
Figure 15:
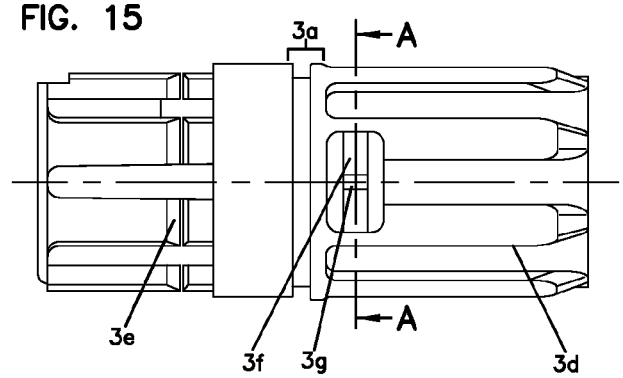
FIG. 15 depicts the mechanism holder of FIG. 14.

FIGS. 14 to 16 show the mechanism holder 3 of the second embodiment in a perspective representation, a side view and in the cross-section A-A indicated in the side view. As in the first embodiment, the mechanism holder 3 is embodied as a one-part sleeve part, preferably as a plastic injection molded part. It comprises a bulge 3e on the outer surface of a front sleeve section. The front sleeve section is plugged into the reservoir part 1 and locked non-detachably, at least for the user, to the reservoir part 1 by means of the bulge 3e.

The latching element 3a is formed on a middle sleeve section of the mechanism holder 3, as in the first embodiment.

A rear sleeve section, connected to the latching element 3a, forms a plurality of axial guides 3d on its outer circumference. The axial guides 3d are formed by guide ribs which protrude radially on the outer circumference of the rear sleeve section. More precisely, the axial guide formed by the axially extending, straight side walls of said guide ribs, such that—as in the first embodiment—axial guiding channels are obtained. The guide ribs protrude out from the middle sleeve section like fingers, as far as the rear end of the mechanism holder 3, where they taper off axially. The axial guide 3d serves to linearly guide the rear casing section 11 when the reservoir module 10 is connected to the dosing and activating module 30. As can be seen in FIG. 9 and most clearly in FIG. 11, engagement elements 11d project radially inwards from the inner surface area of the rear casing section 11, corresponding in number and adapted in shape. One engagement element 11d protrudes into each of the axial guides 3d and is linearly guided by the axial guide 3d when the front casing section 1' and the rear casing section 11 are slid into each other in order to be connected. In this way, it is ensured that there is no relative rotating between the front casing section 1' and the rear casing section 11 when the engagement, secured against rotating, between the dosing and activating element 32 and the dosage setting member 39 is established in the course of connecting.

Since the guide ribs taper off axially at their rear ends, and the guide channels are thus widened into insertion funnels, centering between the front casing section 1' and the rear casing section 11, for the purpose of connecting, is made easier. The guide ribs also taper off at their ends radially with respect to the surface area of the mechanism holder 3, which makes centering the casing sections 1' and 11 into a rotational angular position pre-set by the axial guide 3d, relative to each other, even easier.

Just as the front casing section 1' and the rear casing section 11 are prevented from rotating relative to each other when sliding them into each other, the dosage setting member 39 is also fixed with respect to its rotational angular position relative to the front casing section 1', the dosage setting member 39 being detachably fixed in order to allow the rotational movement of the dosage setting member 39 necessary for dosing. In order therefore to enable the dosing movement of the dosage setting member 39 on the one hand, but to prevent an undesired dosing movement by establishing the connection between the front casing section 1' and the rear casing section 11, the dosage setting member 39 is fixed by the mechanism holder 3 in discrete rotational angular positions, by means of a releasable locking connection.

FIGS. 17 to 20 show individual representations of the dosage setting member 39. For forming the locking connection, a number of locking recesses 39g are formed on the outer surface area of the dosage setting member 39, distributed in regular separation over the circumference. Each of the locking recesses 39g is formed by a straight, axially extending furrow having a rounded contour running in its cross-section.

The mechanism holder 3 is provided with two locking projections 3g (FIGS. 15 and 16). The two locking projections 3g project radially inwards from an inner surface area of the mechanism holder 3 in the rear sleeve section of the mechanism holder 3. They are arranged diametrically opposed to each other. The respective surface region of the mechanism holder 3, on which one of the locking projections 3g is formed, forms a spring element 3f which is elastically flexible in the radially direction. Due to the elastic flexibility and the rounded shape of the locking projections 3g, in conjunction with the rounded profile of the locking recesses 39g, the locking engagement between the locking projections 3g and the opposing locking recesses 39g may be released. This is necessary for selecting the dosage. On the other hand, the locking engagement is however designed such that the dosage setting member 39 is rotationally angularly fixed sufficiently stable that there cannot be any undesired dosing movement of the dosage setting member 39 when the front casing section 1' and the rear casing section 11 are connected, when the rotational coupling between the dosing and activating element 32 and the dosage setting member 39 is established. The locking connection between the mechanism holder 3 and the dosage setting member 39 has the advantageous side effect of a tactile signal during dosing. In order to maintain the favorable elasticity of the spring element 3f, the rear sleeve section of the mechanism holder 3 is cut away in the surface region in question, such that the spring element 3f is maintained as an annular segment extending in the circumferential direction which is axially free on both sides.

Figure 17:
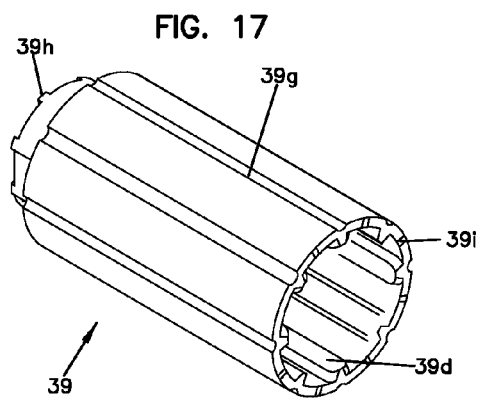
FIG. 17 depicts the dosage setting member of the second embodiment, in a perspective representation.
Figure 18:
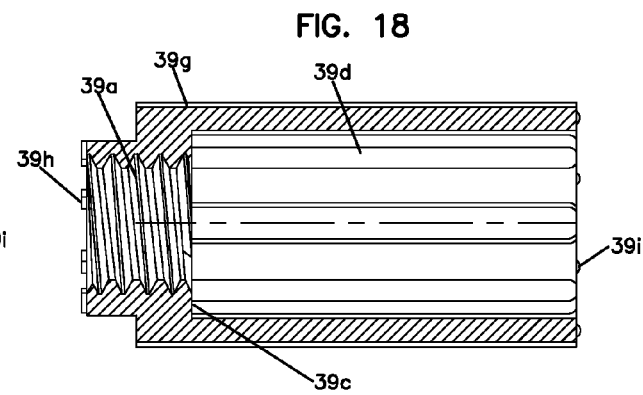
FIG. 18 depicts the dosage setting member of FIG. 17, in a longitudinal section.
Figure 20:
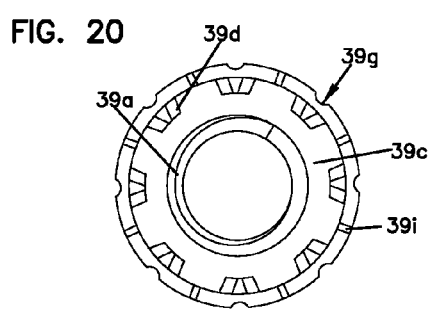
FIG. 20 depicts the dosage setting member of FIG. 17, in a top view.
Figure 19:
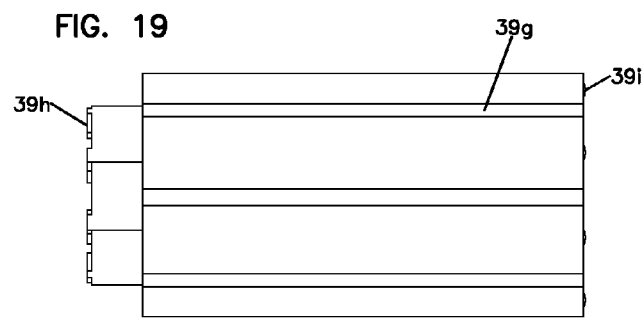
FIG. 19 depicts the dosage setting member of FIG. 17.

Axial guides 39d for the engagement, secured against rotating, between the dosage setting member 39 and the dosing and activating element 32 may likewise be seen in FIGS. 17, 18 and 20. The dosing and activating element 32 is provided with at least one engagement element, in order to obtain the axial linear guide, i.e., the rotational block, between the dosing and activating element 32 and the dosage setting member 39. The axial guides 39d are again guide channels formed by a number of guide ribs extending axially in a straight line. Each of the guide ribs tapers off axially and radially at its rear end facing the dosing and activating element 32, in order to make centering between the dosing and activating element 32 and the dosage setting member 39 easier, when the engagement, secured against rotating, is established. The same design is therefore used for the axial linear guide of the dosage setting member 39 and the dosing and activating element 32 as for the axial linear guide of the casing sections 1' and 11.

For the sake of completeness, reference is lastly also made to the dosing thread 39a and the delivery stopper 39c of the dosage setting member 39, which can most clearly be seen in FIG. 18.

Figure 22:
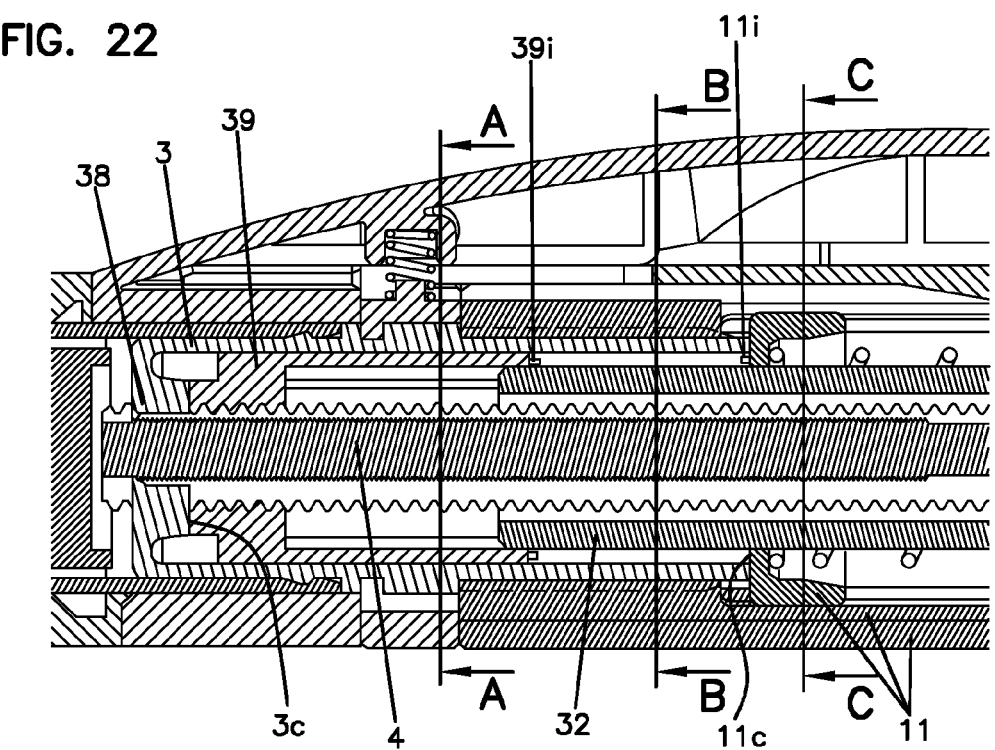
FIG. 22 depicts a portion of the injection apparatus in accordance with FIG. 9.

Lastly, two rotational blocks are provided for the dosage setting member 39 which are active in the two axial end positions of the dosage setting member 39. Reference is additionally made in this regard to FIG. 22.

In order to prevent the possibility of the piston rod 4 being moved back in response to a rotational dosing movement by the dosage setting member 39, rotational stoppers 39h are formed at a front end of the dosage setting member 39. In the front position, which the dosage setting member 39 assumes directly after the product is delivered or before the dosage is selected, the rotational stoppers 39h engage with rotational counter stoppers 3h formed on the mechanism holder 3 (FIG. 16). The rotational stoppers 39h axially project from a front abutting side of the dosage setting member 39, and the rotational counter stoppers 3h protrude from an axially facing abutting area of the mechanism holder 3 forming the delivery stopper 3c, axially opposed to the rotational stoppers 39h. The engagement between the rotational stoppers 39h and the rotational counter stoppers 3h is such that it allows a rotational dosing movement in a rotational direction, which causes a translational dosing movement of the dosage setting member 39 directed away from the delivery stopper 3c, but prevents a rotational dosing movement in the opposite rotational direction, in the front axial end position.

Furthermore, another pair of rotational stoppers and rotational counter stoppers is provided, which are formed and cooperate in basically the same way as the stoppers 3h and 39h. Said second pair of rotational stoppers are rotational stoppers 39i on the one hand, which axially project from a rear abutting area of the dosage setting member 39, and rotational counter stoppers 11i on the other, which axially protrude from the facing stopper abutting area of the rear translational stopper 11c towards the dosage setting member 39, which however cannot be seen in FIG. 9 due to their small dimensions. In the rear end position, the rear pair of rotational stoppers 11i/39i prevents the possibility of the piston rod 4 being moved in the advancing direction in response to a dosing movement by the dosage setting member 39, directed against the rear translational stopper 11c.

The height, i.e., the axial length, of all the rotational stoppers 3h, 39h, 11i and 39i is adjusted to the thread pitch of the engaged dosing thread of the piston rod 4 and the dosage setting member 39. The rotational stoppers are axially sufficiently short that the rotational dosing movement which moves the dosage setting member 39 away from the respective translational stopper 3c or 11c is not impeded.

When assembling the components of the reservoir module 10, the dosage setting member 39 is screwed onto the piston rod 4 as far as a pre-set axial position, as may be seen from FIG. 9. The piston rod 4, together with the screwed-on dosage setting member 39, is then inserted into the mechanism holder 3 from behind, until its blocking means 38 comes into blocking engagement with the returning blocking means 6 of the piston rod 4 and furthermore the engagement, secured against rotating, between the rotational stoppers 39h of the dosage setting member 39 and rotational counter stoppers of the mechanism holder 3 is established. Even while being inserted into the mechanism holder 3, the dosage setting member 39 is axially and linearly guided by the mechanism holder 3 via the locking engagement between the locking projections 3g and the locking recesses 39g, until the dosage setting member 39 abuts the delivery stopper 3c of the mechanism holder 3. In this front end position of the dosage setting member 39 relative to the mechanism holder 3, the engagement, secured against rotating, between the rotational stoppers 3h and 39h has also already been established.

In this state, the mechanism holder 3 and a reservoir part 1, already fitted with a reservoir, are connected to each other.

In a following step, the rear casing section 11 of the completely assembled dosing and activating module 30 is slid onto the mechanism holder 3, wherein the mechanism holder 3 and the rear casing section 11 can be centered with respect to each other due to the axial guides 3d and the engagement elements 11d of the rear casing section 11 and, once centered, are axially and linearly guided onto each other due to the guide engagement. In the course of sliding the rear casing section 11 onto the mechanism holder 3, the dosing and activating element 32 comes into engagement, secured against rotating, with the dosage setting member 39, wherein here too a certain centering is also possible first, using a linear guide corresponding to the axial guides 3d and the engagement elements 11d.

The dosing and activating element 32 is in locking engagement with the rear casing section in discrete rotational angular locking positions and in the locking engagement, i.e., in the respective rotational angular locking position, is axially and linearly guided. The rotational angular difference between two consecutive rotational angular locking positions corresponds to one dosage unit. The linear guide between the mechanism holder 3 and the rear casing section 11 on the one hand, and the discrete rotational angular positions of the dosage setting member 39 relative to the mechanism holder 3 (locking projections 3g and locking recesses 39g) and the rotational angular locking positions of the dosing and activating element 32 relative to the rear casing section 11 on the other, are adjusted to each other such that the two casing sections 1' and 11 are always slid linearly over each other in a rotational angular position such that the dosage setting member 39 and the dosing and activating element 32 are also aligned relative to each other for their engagement, secured against rotating, such that there is no relative rotating between the components involved in dosing while the reservoir module 10 is connected to the dosing and activating module 30.

With respect to the other details of assembling, in particular of establishing the latching engagement, and of the functionality or operation of an injection apparatus in accordance with the second embodiment, reference is made to the description of first embodiment.

Figure 21:
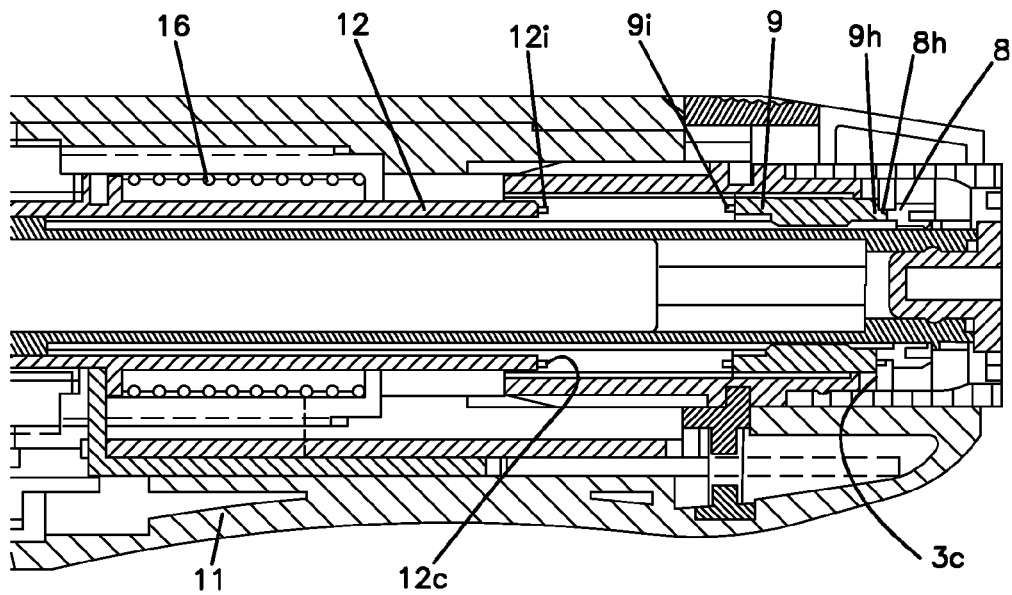
FIG. 21 depicts a portion of the injection apparatus in accordance with FIG. 3.

Rotational blocks can also be provided in the injection apparatus in accordance with the first embodiment, which prevent undesired response movements by the piston rod 4 in the two axial end positions of the dosage setting member 9 of the first embodiment. FIG. 21 shows the two rotational blocks, which are formed in the same way as the rotational blocks of the second embodiment. However, the rotational counter stoppers which in the second embodiment are formed on the casing sections 1' and 11 are formed in the first embodiment by the blocking means 8 on the one hand and the dosing and activating element 12 on the other. Thus, a number of rotational stoppers 8h are formed on the abutting side of the blocking means 8 axially facing the dosage setting member 9 and axially protrude towards the dosage setting member 9. Since the blocking means 8 is axially and immovably mounted by the front casing section 1' and connected, secured against rotating, to the piston rod 4, a rotational block for the rotational dosing movement between the piston rod 4 and the dosage setting member 9 is also obtained, via the front pair of rotational stoppers 8h/9h. The second pair of rotational stoppers is formed between the dosage setting member 9 and the rear translational stopper 12c. As in the second embodiment, a number of rotational stoppers 12i protrude axially towards the dosage setting member 9 from the abutting area of the translational stopper 12c axially facing the dosage setting member 9. As in the second embodiment, the dosage setting member 9 is provided on its rear side with rotational stoppers 9i which in the rear axial end position of the dosage setting member 9 engage with the rotational stoppers 12i. In the rear axial end position of the dosage setting member 9, the rear pair of rotational stoppers 9i/12i only allows the rotational dosing movement which causes a translational dosing movement of the dosage setting member 9 in the advancing direction.

In the foregoing description, embodiments of the present invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:
1. A semi disposable product dispensing apparatus comprising a disposable reservoir module and a reusable dosing and activating module which are detachably connected to each other,
   said disposable reservoir module comprising:
   a) a front casing section which comprises a reservoir for a product which can be delivered and a first connecting means;
   b) a piston accommodated in said reservoir such that it can be shifted in a dispensing direction towards a reservoir outlet to deliver the product, and
   c) a piston rod moveable in and against the dispensing direction; and
   said reusable dosing and activating module comprising:
   a) a rear casing section including a second connecting means engageable with the first connecting means to form a detachable connection;
   b) a dosing and drive element which is in a releasable engagement with the piston rod of the disposable reservoir module for providing and performing a dosing and delivery movement for delivery of the product;
   c) a motor for performing the delivery movement of the dosing and drive element, and
   d) a dose slaving means which is axially and rotationally fixed to the dosing and drive element wherein the piston rod comprises a connecting section which engages with the dose slaving means such that the piston rod and the dosing and drive element cannot be rotated relative to each other but can be moved relative to each other along the longitudinal axis in and counter to the advancing direction.

2. The product dispensing apparatus as set forth in claim 1, wherein the disposable reservoir module is disposed of or recycled once the reservoir has been emptied and the dosing and activating module can be repeatedly used with a new reservoir module.

3. The product dispensing apparatus as set forth in claim 1, wherein the product can be injected or infused subcutaneously.

4. The product dispensing apparatus as set forth in claim 1, wherein the product is preferably a liquid for medical, therapeutic, diagnostic pharmaceutical or cosmetic applications.

5. The product dispensing apparatus as set forth in claim 4, wherein the product is insulin or a growth hormone.

6. The product dispensing apparatus as set forth in claim 1, wherein the releasable engagement between the dosing and drive element and the piston rod is a threaded engagement or toothed engagement.

7. The product dispensing apparatus as set forth in claim 1, wherein the reusable dosing and activating module carries the operating components and operating mechanisms.

8. The product dispensing apparatus as set forth in claim 1, wherein the reusable dosing and activating module comprises counting and indicating means for counting and optically indicating a selected product dosage.

9. The product dispensing apparatus as set forth in claim 1, wherein the reservoir module comprises a container accommodated in the front casing or the reservoir is formed by the casing itself.

10. The product dispensing apparatus as set forth in claim 1, wherein the piston rod is permanently connected to the piston by forming an integrated part as one piece.

11. The product dispensing apparatus as set forth in claim 1, wherein the piston rod and piston are embodied as separate components.

12. The product dispensing apparatus as set forth in claim 1, wherein the dosing and activating element is a hollow cylinder that surrounds the piston rod via a front section.

13. The product dispensing apparatus as set forth in claim 1, wherein the dose slaving means is inserted into the dosing and drive element from the rear.

14. The product dispensing apparatus as set forth in claim 1, wherein the piston rod comprises a linear guide for the dose slaving means.

15. The product dispensing apparatus as set forth in claim 1, wherein the connecting section is formed as a linear guide for the dose slaving means.

16. The product dispensing apparatus as set forth in claim 1, wherein the disposable reservoir module comprises a block and the piston rod a return block engageable with the block, which prevents the piston rod from moving against the dispensing direction.

17. The product dispensing apparatus as set forth in claim 1, wherein the dosing and drive element operates manually, semi-automatically or fully automatically.

18. The product dispensing apparatus as set forth in claim 1, wherein the motor is a spring driven motor.

19. The product dispensing apparatus as set forth in claim 1, wherein the piston rod of a new disposable reservoir module extends from the reservoir and the dosing and drive element is hollow and cylindrical and for forming the detachable connection, the piston rod of a new disposable reservoir module has an external geometry for alignment with and insertion into the dosing and drive element.

* * * * *